US010150961B2

(12) United States Patent
Yi et al.

(10) Patent No.: US 10,150,961 B2
(45) Date of Patent: Dec. 11, 2018

(54) METHODS FOR PREPARING MONOCLONAL ANTIBODIES RECOGNIZING GLYCAN BINDING SITE AS AN EPITOPE

(71) Applicants: Seoul National University R&DB Foundation, Seoul (KR); Kangwon National University Industry Cooperation Foundation, Chuncheon, Gangwon-Do (KR)

(72) Inventors: Eugene C. Yi, Seoul (KR); Min Jueng Kang, Seoul (KR); Kristine M. Kim, Gangwon-Do (KR); Eunhee G. Kim, Gangwon-Do (KR)

(73) Assignees: Seoul National University R&DB Foundation, Seoul (KR); Kangwon National University Industry Cooperation Foundation, Chuncheon, Gangwon-do (KR)

( * ) Notice: Subject to any disclaimer, the term of this patent is extended or adjusted under 35 U.S.C. 154(b) by 561 days.

(21) Appl. No.: 13/946,731

(22) Filed: Jul. 19, 2013

(65) Prior Publication Data
US 2014/0162890 A1    Jun. 12, 2014

(30) Foreign Application Priority Data

Jul. 23, 2012 (KR) .................. 10-2012-0080193

(51) Int. Cl.
C40B 30/04    (2006.01)
C12N 15/10    (2006.01)
C12P 21/06    (2006.01)

(52) U.S. Cl.
CPC .......... *C12N 15/1037* (2013.01); *C12P 21/06* (2013.01); *C40B 30/04* (2013.01)

(58) Field of Classification Search
None
See application file for complete search history.

(56) References Cited

PUBLICATIONS

Bender et al. (2007) Journal of Virology vol. 81 pp. 3827 to 3841.*
Stewart Dec. 31, 2011 Journal of Immunological Methods vol. 376 pp. 150 to 155.*
Zhang et al. (2003) Nature Biotechnology vol. 21 pp. 660 to 666.*
Geng et al. (2001) Journal of Chromatography B vol. 752 pp. 293 to 306.*

(Continued)

*Primary Examiner* — Christian C Boesen
(74) *Attorney, Agent, or Firm* — Mintz Levin Cohn Ferris Glovsky and Popeo, P.C.; Kongsik Kim; Katherine Jensen

(57) ABSTRACT

The present disclosure relates to a method for producing a monoclonal antibody that binds to an epitope for the glycan binding site of a glycoprotein. According to the present disclosure, a monoclonal antibody that recognizes the glycan binding site of a glycoprotein as an epitope can be produced in a relatively simple and economic manner, and a monoclonal antibody having high sensitivity and specificity for the glycan binding site of a glycoprotein can be produced. The monoclonal antibody produced according to the present disclosure can be effectively used as an agent for diagnosing or treating various diseases associated with a change in glycan structure or glycan expression level.

9 Claims, 17 Drawing Sheets

(56) References Cited

PUBLICATIONS

Kim et al. (Mar. 16, 2012) PLoS One vol. 7 article e33322 pp. 1 to 15.*
Morelle 2007 Nature Protocols vol. 2 pp. 1585 to 1602.*
Calarese et al. (Jun. 27, 2003) Science vol. 300 pp. 2065 to 2071.*
Calarese et al. (Sep. 20, 2005) Proceedings of the National Academy of Sciences USA vol. 102 pp. 13372 to 13377.*
Ahn, Hyun Joo et al., "Generation of antibodies recognizing an aberrant glycoform of human tissue inhibitor of metalloproteinase-1 (TIMP-1) using decoy immunization and phage display" Jrl. of Biotechnology, 151 (2001) 225-230.
Tian, Y. et al., "Solid-phase extraction of N-linked glycopeptides", Nature Protocols, vol. 2, No. 2 (2007) pp. 334-339.
Korean Office Action for Korean Patent Application No. 10-2012-0080193, dated Aug. 21, 2018, English translation, 9 pages.

* cited by examiner

METHODS FOR PREPARING MONOCLONAL ANTIBODIES RECOGNIZING GLYCAN BINDING SITE AS AN EPITOPE

CROSS REFERENCE TO RELATED APPLICATION

The present application claims priority to Korean Application No. 10-2012-0080193 filed on Jul. 23, 2012, which is incorporated herein by reference.

TECHNICAL FIELD

The present disclosure relates to a method for preparing a monoclonal antibody that recognizes a glycan site of a glycoprotein as an epitope.

BACKGROUND ART

A glycoprotein is a protein containing carbohydrate residue(s) in addition to the polypeptide chain where the protein/sugar complex is formed by covalent bonding with sugar by glycosylation of the amino acid residue of the protein during the post-translational modification of the protein. It is known that the glycosylation of a protein is catalyzed by N-acetylglucosaminyltransferase and that the complex carbohydrates of a glycoprotein are synthesized in which monosaccharides are sequentially transferred to the amino acid residues (such as serine, threonine and asparagine) of the protein resulting in the generation of the glycoprotein.

Glycosylation of a protein is divided into N-linked glycosylation, which occurs through the asparagine side-chain of a glycosylation consensus sequence consisting of amino acid-serine-threonine (NXS/T) excluding asparagine-proline during the protein synthesis, and O-linked glycosylation which occurs through a hydroxyl group of serine or threonine residues. In addition, glycans that are commonly found in glycoprotein include glucose (Glc), galactose (Gal), mannose (Man), fucose (Fuc), N-acetylgalactosamine (GalNAc), N-acetylglucosamine (GlcNAc) and N-acetylneuraminic acid (NeuNAc) (Frank Kjeldsen, et al. Anal. Chem. 2003, 75, 2355-2361).

It is known that the sugar chains of many kinds of glycoproteins present on the cell surface are involved in many of the basic phenomena of multicellular processes, including intercellular recognition and adhesion in the modification, development and differentiation processes including the induction of differentiation of immune and neural cells, infection of host cells by bacteria and viruses, adhesion of toxins to cells, cell carcinogenesis and cancer metastasis, and the like.

In addition, the difference in the glycosylation of a glycoprotein can be an important clinical index to distinguish the effect of a targeted therapeutic agent or resistance to the therapeutic agent. For example, according to Kim J G et al. (2012). "Heterodimerization of glycosylated insulin-like growth factor-1 receptors and insulin receptors in cancer cells sensitive to anti-IGF1R antibody"; PLoS One; 7(3): e33322, it is known that resistance to an anticancer therapeutic agent in liver cancer is associated with a change in N-linked glycosylation.

Thus, studies on the difference in the glycosylation of a glycoprotein make it possible to predict the prognosis of disease and obtain information for therapeutic responses to predict the effect of a target therapeutic agent.

Accordingly, antibodies that target the sugar chains of a glycoprotein have recently been studied and developed. For example, a method for developing an antibody that targets sugar chains has been proposed, which comprises immobilizing a chemically synthesized glycan onto a plate and screening an antibody that binds specifically to the glycan (Blixt, O., S. Head, et al. (2004). "Printed covalent glycan array for ligand profiling of diverse glycan binding proteins." Proc Natl Acad Sci USA 101(49): 17033-17038). However, the antibody selected by the above method targets the chemically synthesized glycan, and thus the actual application of the antibody to sugar chains bound to proteins such as glycoprotein in vivo was limited.

Accordingly, the inventors in the present invention have invented a method for producing a novel antibody, which comprises proteolyzing a glycoprotein obtained from a biological sample to extract short-length glycopeptide(s) containing a glycan and applying a phage antibody display method to the glycopeptide(s), thereby completing the present disclosure.

SUMMARY

The object of the present disclosure is to provide a method capable of efficiently producing monoclonal antibodies that recognize the glycan binding site of a glycoprotein as an epitope.

The present disclosure provides a method for producing monoclonal antibodies that recognize the glycan binding site of a glycoprotein as an eptiope comprising the steps of: a) proteolyzing the glycoprotein to obtain (poly)peptide fragments; b) subjecting a mixture of the (poly)peptide fragments to treatment with hydrazide beads or hydrazide nanoparticles to capture a glycan-containing glycopeptide; and c) identifying a monoclonal antibody, which binds specifically to the captured glycopeptide, using a peptide, a protein including a antibody or a scaffold library.

DETAILED DESCRIPTION

Figure 1:
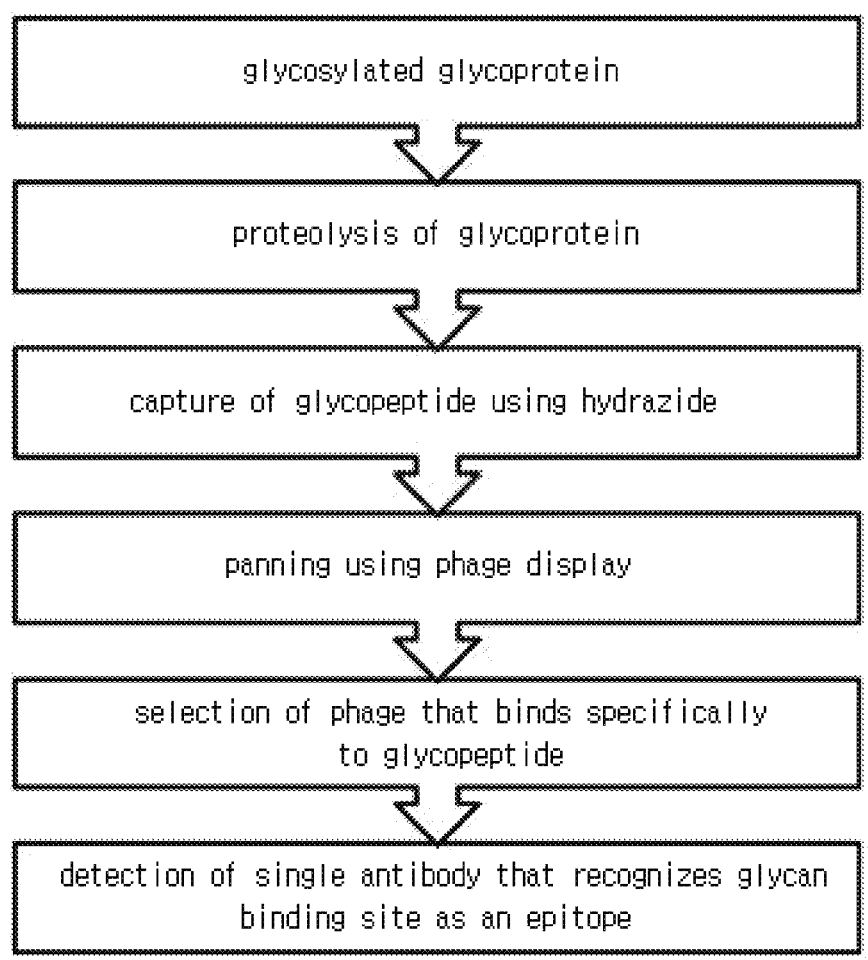
FIG. 1 is a flowchart showing a method for producing monoclonal antibodies that recognize the glycan binding site of a glycoprotein as an epitope according to the present disclosure.
Figure 2:
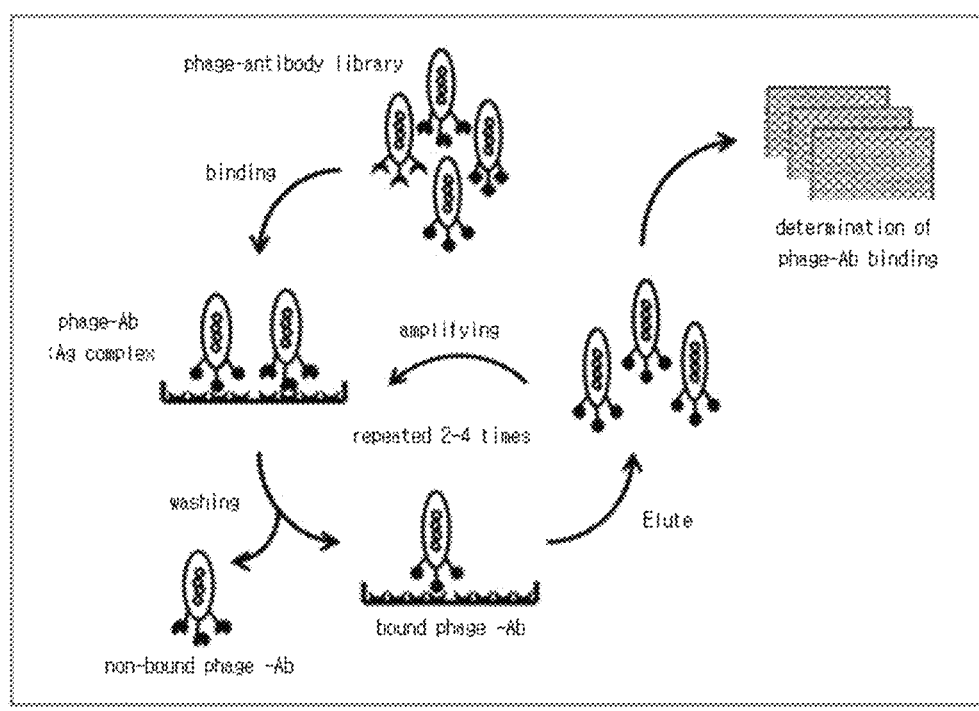
FIG. 2 is a schematic presentation showing a panning method that uses a phage antibody display to identify and select antibody according to the present disclosure.

The present disclosure provides a method for producing monoclonal antibodies that recognizes as an epitope the glycan binding site of a glycoprotein, the method comprising the steps of: a) proteolysis the glycoprotein to obtain (poly) peptide fragments and oxidizing N-linked glycans thereof; b) subjecting a mixture of the (poly) peptide fragments to treatment with hydrazide beads or hydrazide nanoparticles to capture a glycan-containing glycopeptide; and c) identifying a monoclonal antibody, which binds specifically to the captured glycopeptide, using a peptide, protein or scaffold library.

The present disclosure relates to a method for producing monoclonal antibodies that recognize the peptide-bound glycan binding site of a glycoprotein as an epitope and responds specifically thereto. According to the method of the present disclosure, an antibody that specifically recognizes only a specific glycoprotein or a specific glycan binding site in various biological materials can be effectively produced.

As used herein, the phrase "glycan binding site of a glycoprotein" refers to the glycan bound to the (poly)peptide and a part of a peptide-glycan binding site of a glycoprotein. Specifically, the glycan binding site of the glycoprotein may mean a binding point at which the peptide and glycan of the glycoprotein are bound to each other, or a peptide or glycan region near the binding point, or a region comprising both the binding point and the peptide or glycan region. Herein, the peptide region near the binding point may be, for example, a 1-50 amino acid peptide region, a 1-20 amino acid peptide region, a 1-15 amino acid peptide region, a 1-10 amino acid peptide region or a 1-5 amino acid peptide region, which comprises the amino acid of the binding point at which the peptide and glycan of the glycoprotein are bound to each other, but is not limited thereto. In addition, the glycan region near the binding point may be, for example, a glycan region comprising a monosaccharide or oligosaccharide bound to the binding point, but is not limited thereto.

As used herein, the phrase "monoclonal antibody that recognizes the glycan binding site of a glycoprotein as an epitope" refers to a monoclonal antibody that recognizes as an epitope the glycan binding site of a glycoprotein and binds specifically thereto.

In an embodiment of the present disclosure, the glycan binding site of a glycoprotein may be an N-linked glycan binding site glycosylated at the asparagine side-chain of a glycosylation consensus sequence, which consists of amino acid-serine-threonine (NXS/T) excluding asparagine-proline, in a process in which the protein is made in vivo or in vitro.

In another embodiment of the present disclosure, the glycan structure or expression level of a glycan of the glycoprotein can be changed depending on the diagnosis of a disease and resistance of a disease to a therapeutic agent. According to the present disclosure, an antibody can be produced that targets the glycan binding site of a glycoprotein that can be changed in terms of the glycan structure or expression level of a glycan depending on the diagnosis of a disease, the resistance of a disease to an agent for treating the disease, and thus the method of the present disclosure can be effectively used for the research, diagnosis or treatment of disease.

For example, in the case in which the glycosylation of a specific glycoprotein is not observed or observed in a very low level in a normal group, but is observed only or in a significantly higher level in the glycoprotein of a specific disease group, an antibody that targets the glycoprotein can be developed and used to diagnose or treat the specific disease. Further, in the case in which the glycosylation of a glycoprotein differs in the state of a specific disease, an antibody that targets the glycoprotein can be developed and used to diagnose the state of the disease. In addition, in the case in which the glycosylation of a specific glycoprotein becomes the cause of resistance to an agent for treating disease, an antibody that targets the glycoprotein can be developed and used to remove the cause of resistance to the therapeutic agent.

The disease-related glycoprotein may be, for example, a glycoprotein derived from cancer cells. Examples of the cancer include, but are not limited to, brain cancer, esophageal cancer, lung cancer, stomach cancer, liver cancer, colorectal cancer, rectal cancer, pancreatic cancer, prostate cancer, bladder cancer, testicular cancer, breast cancer, uterine cancer, ovarian cancer, leukemia and the like. In addition, the glycoprotein may be, in addition to a cancer cell-derived glycoprotein, a protein such as epidermal growth factor receptor (EGFR) or hepatocyte growth factor receptor c-Met, which is a protein targeted by anticancer agents and is highly expressed specifically in disease.

However, the characteristic of the present disclosure is not limited to the kind of glycoprotein, and the kind of protein that is targeted by the antibody can be easily selected by those skilled in the art depending on the intended use.

Hereinafter, each step of the method for producing the monoclonal antibody according to the present disclosure will be described in detail.

The glycoprotein that is used in the present disclosure may be extracted from a biological sample. When the glycoprotein is extracted from a biological sample, it can be extracted using a method known in the art, such as a BCA (bicinchoninic acid) method, an immunoprecipitation method or the like.

Step a) of the method of the present disclosure is a step of proteolyzing the glycoprotein. According to an embodiment of the present disclosure, step a) may be performed by subjecting the glycoprotein to treatment with proteinase or a proteinase reagent. Herein, the proteinase may be selected from the group consisting of pepsin, trypsin, chymotrypsin, peptidase, and endoproteinase GluC, and the proteinase reagent may be cyanogen bromide (CNBr). A suitable enzyme or reagent and proteolysis conditions can be suitably selected by those skilled in the art, and the characteristic of the present disclosure is not limited to a specific kind of proteinase or reagent.

In another embodiment of the present disclosure, in order to efficiently proteolyze the glycoprotein to make a mixture of (poly) peptide fragments, the glycoprotein may be subjected to generally known pretreatment processes such as denaturation, reduction and alkylation.

In another embodiment of the present disclosure, the method may further comprise, between steps a) and b), a step of desalting the (poly) peptide fragments obtained by proteolysis in step a). When this desalting process is performed, salts can be removed from the (poly) peptide fragments, thereby preventing such salts from interfering with a process of capturing a glycan-containing glycopeptides. The desalting method that is used in the present disclosure is not specifically limited, and any desalting method known in the art may be suitably selected by those skilled in the art. For example, the (poly) peptide fragments may be desalted by a chromatographic method using a C-18 packed column, but is not limited thereto.

Step b) of the method of the present disclosure is a step of capturing a glycopeptide using a hydrazide group. In this step, only glycan-containing glycopeptides are selected using the principle in which, when the hydroxyl group attached to a carbon atom at the terminus of glycan is oxidized to aldehyde, the aldehyde forms a covalent bond with a hydrazide group (see B. Sun et al. Molecular & Cellular Proteomics 6, 141 (2007)).

Thus, according to an embodiment of the present disclosure, the method may further comprise, before step b) of capturing a glycopeptide, a pretreatment step of oxidizing the (poly) peptide fragments obtained by proteolysis in step a). The method of oxidizing the (poly) peptide fragments is not specifically limited, as long as it is a method by which the hydroxyl group attached to a carbon atom at the terminus of the glycan of a glycan-containing glycopeptide among the (poly) peptide fragments can be oxidized to aldehyde. Any oxidation method known in the art may be suitably selected by those skilled in the art. For example, the terminus of glycan of a glycan-containing glycopeptide among the (poly) peptide fragments can be oxidized by subjecting a mixture of the (poly) peptide fragments to treatment with sodium meta-periodate ($NaIO_4$), but is not limited thereto.

According to another embodiment of the present disclosure, before the (poly) peptide fragments are bound to hydrazide-terminated beads or nanoparticles in the method, the (poly) peptide fragments may also be desalted or buffer-exchanged in order to prevent the excessive oxidation of the (poly) peptide fragments.

As used herein, the term "hydrazide beads" refers to hydrazide-terminated beads, and the term "hydrazide nanoparticles" refers to hydrazide-terminated nanoparticles. According to another embodiment of the present disclosure, the hydrazide beads that are used in step b) may be hydrazide-terminated magnetic beads or hydrazide-terminated Sepharose beads.

For example, when the hydrazide beads are magnetic beads, a mixture of the (poly) peptide fragments is treated with hydrazide-terminated magnetic beads to form a complex of the glycopeptides and the hydrazide beads, and then the magnetic beads are attached to the edge of a tube using a magnetic separator, and the floating solution is removed. Then, the resulting material is washed by repeatedly adding and removing different solvents such as water, NaCl, methanol and acetonitrile, whereby only a glycopeptide-hydrazide bead complex can be captured. The solvents that are used herein are not specifically limited and can be suitably selected by those skilled in the art. When this method is used, only the complex can be easily separated from the mixture of the (poly) peptide fragments.

For example, when the hydrazide beads are Sepharose beads, the glycopeptide can be separated by either a filtration method using a spin column or a method of precipitating the beads in the tube by centrifugation and removing only the supernatant.

The hydrazide-terminated magnetic beads, or the Sepharose beads or the hydrazide-terminated nanoparticles are commercially available or can be chemically synthesized by any method known in the art. A specific example of the method for capturing the glycopeptide using hydrazide-terminated magnetic beads is disclosed in Zhang et al. Nature Biotechnology 21(6) 2003.

Step c) of the method of the present disclosure is a step of isolating a monoclonal antibody that recognizes the glycan binding site of the glycopeptide, captured in step b) as an epitope, using a peptide, protein or scaffold library.

In an embodiment of the present disclosure, the peptide, protein or scaffold library may be selected from the group consisting of a phage display, a yeast display, a bacterial display and a ribosome display. The above phage display, yeast display, bacterial display and ribosome display methods are well known in the art.

For example, the "phage display method" is a method which comprises inserting, replacing or fusing foreign peptides (variable domain of antibody) into the capsid protein of a bacteriophage to display the foreign peptides (antibodies) on the phage surface, which are collectively referred to as phage antibody, and detecting the target of interest that binds specifically to the fusion peptides (antibodies) displayed on the phage surface. The phage display method is well known as a method for identification and isolation of an antibody that binds to a specific antigen of interest.

For example, when the phage display method is used, step c) comprises: a step of panning the glycopeptide, captured in step b), with a phage displaying a total antibody, a heavy-chain variable domain, a light-chain variable domain, scFv, Fab, dsFv or the like; and selecting a phage antibody that binds to the antigen such as glycopeptides. As used herein, the term "panning" refers to a process of removing phage antibodies that do not bind to a specific antigen, recovering phage antibodies that bind to the antigen, and transfecting the recovered phage antibodies into E. coli to amplify the number of phage antibodies. When the panning process is repeated, a phage antibody that specifically recognizes the glycan binding site of glycoprotein can be easily identified and selected.

The step of selecting a monoclonal antibody, which recognizes the glycan binding site as an epitope, from the selected phage antibodies, can be performed using any detection method known in the art.

A monoclonal antibody that recognizes the glycan binding site as an epitope can be determined and isolated from the selected phage antibodies using various analysis methods. For example, an antibody or a phage antibody can be obtained by spreading the phage antibodies, which bind to a glycan, on an agar plate, and collecting each isolated monoclonal phage antibody clone. Whether each antibody or phage antibody binds specifically to glycan binding site can be determined by an ELISA method, and a monoclonal antibody that specifically binds to a glycan binding site can be selected and identified by sequencing the DNA of each phage antibody.

In another embodiment of the present disclosure, the method may further comprise a step of determining whether the monoclonal antibody obtained in step c) specifically recognizes the glycan binding site of the glycoprotein.

Specifically, the step of binding the produced phage antibody or monoclonal antibody to a glycan-containing specific glycoprotein and a control protein obtained by removing the glycan from the glycoprotein to leave a (poly)peptide region can be performed to determine whether the phage antibody or monoclonal antibody binds to the glycoprotein with specificity for a glycan binding site. When the produced monoclonal antibody binds to the glycan-containing specific protein, but does not bind to the control protein obtained by removing the glycan, the produced phage antibody or monoclonal antibody can be determined to be an antibody that specifically recognizes the glycan binding site of the specific glycoprotein. The method of producing the control protein by removing the glycan from the glycoprotein to leave only the peptide region is known in the art. For example, the glycan binding site can be removed from the glycoprotein by a suitable enzyme.

In another embodiment, the step of determining the monoclonal antibody can be performed by expressing a glycoprotein, which contains an epitope that is targeted by the produced monoclonal antibody, in E. coli or an in vitro cell-free expression system, and mammalian cells, binding the produced monoclonal antibody to the expressed proteins, and determining whether the monoclonal antibody binds to the glycoprotein. In *E. coli* cells or the in vitro cell-free expression system, glycosylation cannot occur during protein synthesis, and thus a glycan-containing glycoprotein cannot be synthesized, whereas in mammalian cells, glycosylation occurs during protein synthesis so that a glycan-containing glycoprotein is synthesized. Thus, when the monoclonal antibody produced according to the present disclosure does not bind to the protein expressed in *E. coli* cells or the in vitro cell-free system, but binds specifically to the glycoprotein expressed in mammalian cells, the produced monoclonal antibody can be determined to be a monoclonal antibody that recognizes the glycan binding site of the glycoprotein as an eptiope.

Hereinafter, the present disclosure will be described in detail with reference to examples. It is to be understood, however, that these examples are for illustrative purposes only and are not intended to limit the scope of the present disclosure. The examples of the present disclosure are provided to more completely explain the present disclosure to those of ordinary skill in the art.

Example 1: Production of a Monoclonal Antibody that Recognizes the N-Linked Glycan Binding Site of c-Met as an Eptiope 1-1: Proteolysis of c-Met In order to proteolyze c-Met protein into peptides, a dissolved sample was denatured with 6M urea at room temperature, and then DTT was added thereto to reduce disulfide bonds. Then, iodoacetamide was added thereto, and the alkylation of sulfhydryl groups was performed at room temperature under dark conditions. The sample was diluted so that the final concentration of urea was 1M or less, and the sample was reacted with trypsin at a trypsin: sample ratio of 1:50 at 37° C. The peptides were desalted using a C18 reverse phase cartridge (Waters), eluted with formic acid and acetonitrile, and dried with Speed Vac, thereby obtaining a c-Met peptide mixture.

1-2: Capture of Glycopeptide Using Hydrazide Magnetic Beads

In order to oxidize a hydroxyl group, attached to a carbon atom at the terminus of the glycan of a glycan-containing glycopeptide in the mixture of the c-Met (poly) peptide fragments, to aldehyde, the mixture was treated with sodium meta-periodate ($NaIO_4$) to a final concentration of 10 mM and then rotated at room temperature for 1 hour under dark conditions. Then, the mixture of the (poly) peptide fragments was desalted with a C-18 reverse phase cartridge, re-suspended in 0.1 M sodium acetate buffer (pH 5.6), treated with hydrazide-terminated magnetic beads, and rotated at room temperature for 12-14 hours. As a c-MET glycopeptides-hydrazide bead complex was formed, a suspension containing peptides which were not bound to the magnetic beads was removed using a magnetic separator. The remaining material was sequentially washed by repeatedly adding and removing 1M NaCl, 80% acetonitrile and HPLC water. In order to determine whether the glycopeptide was captured using the magnetic beads, a portion of the magnetic beads was taken out, suspended in 50 mM ammonium bicarbonate, treated with PNGase F, and desalted using Oasis MCX (Mixed-mode Cation-eXchange (Waters). The eluted peptide was analyzed by high-performance liquid chromatography-mass spectrometry (LC-MS) to identify the amino acid sequence of the captured peptide and determine the N-linked glycosylation sites.

Figure 3A:
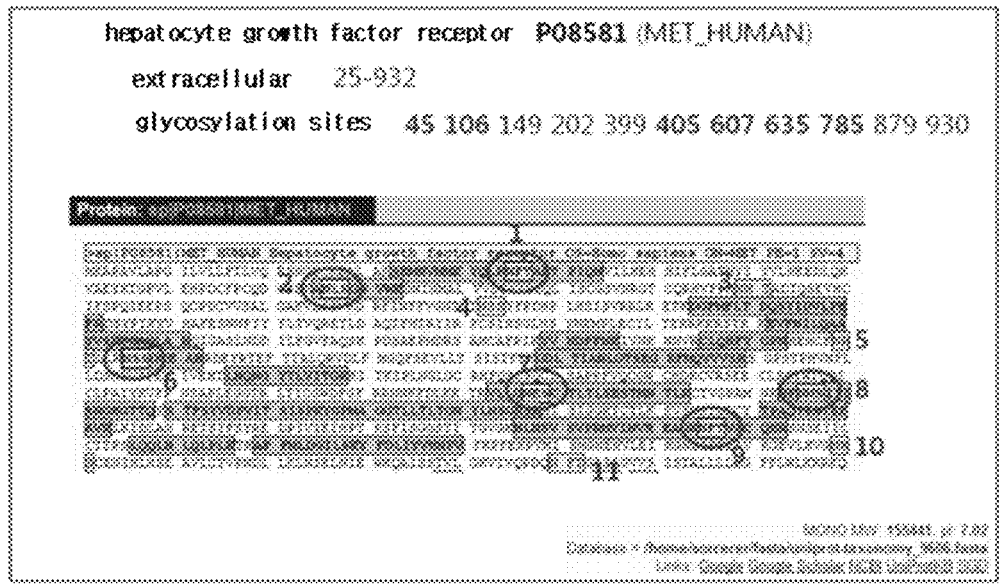
FIGS. 3A through 3F show N-linked glycosylated sites determined by high-performance liquid chromatography-mass spectrometric analysis of c-Met glycopeptides captured using hydrazide beads.
Figure 3B:
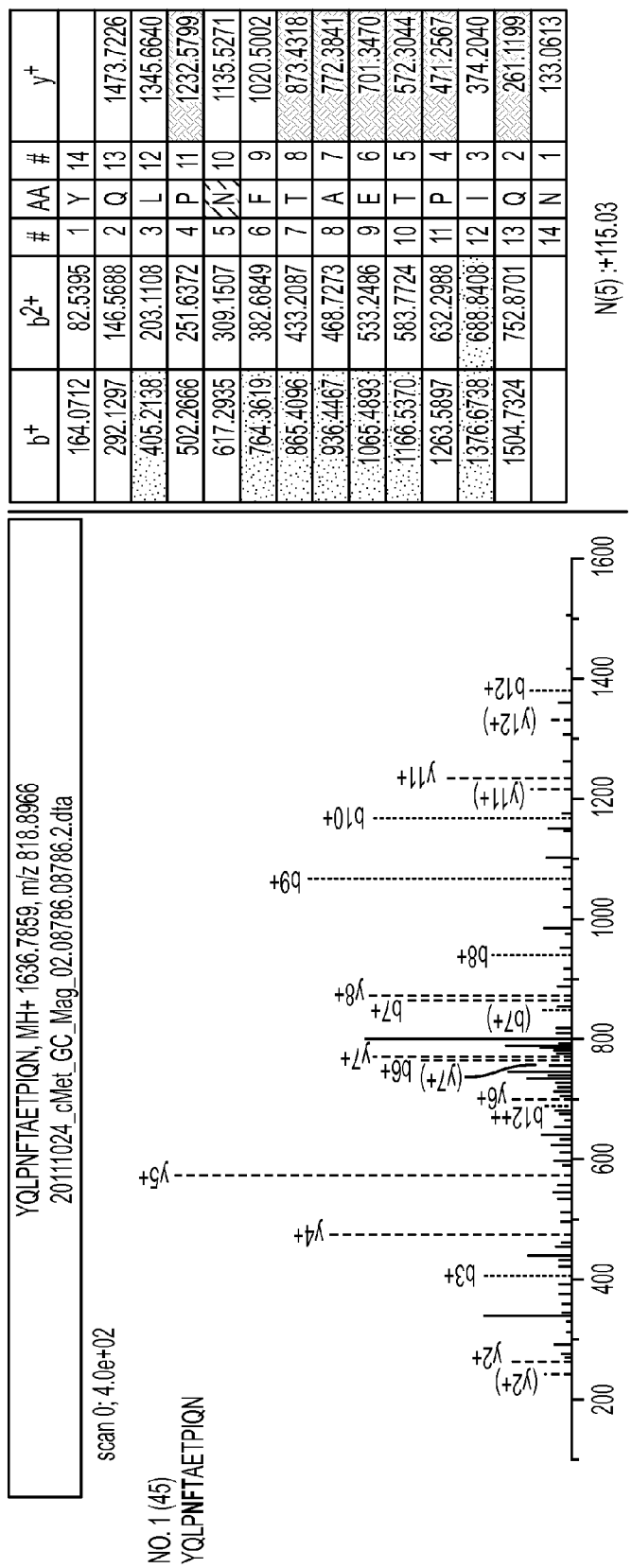
Figure 3C:
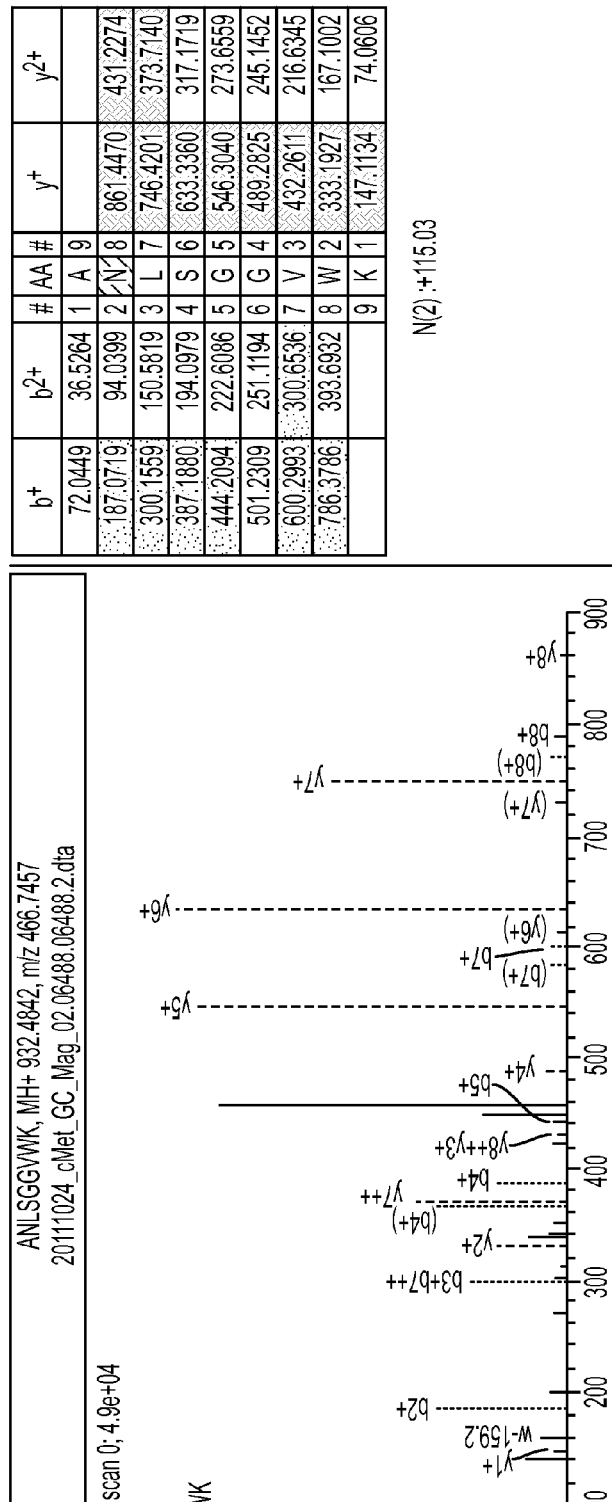
Figure 3D:
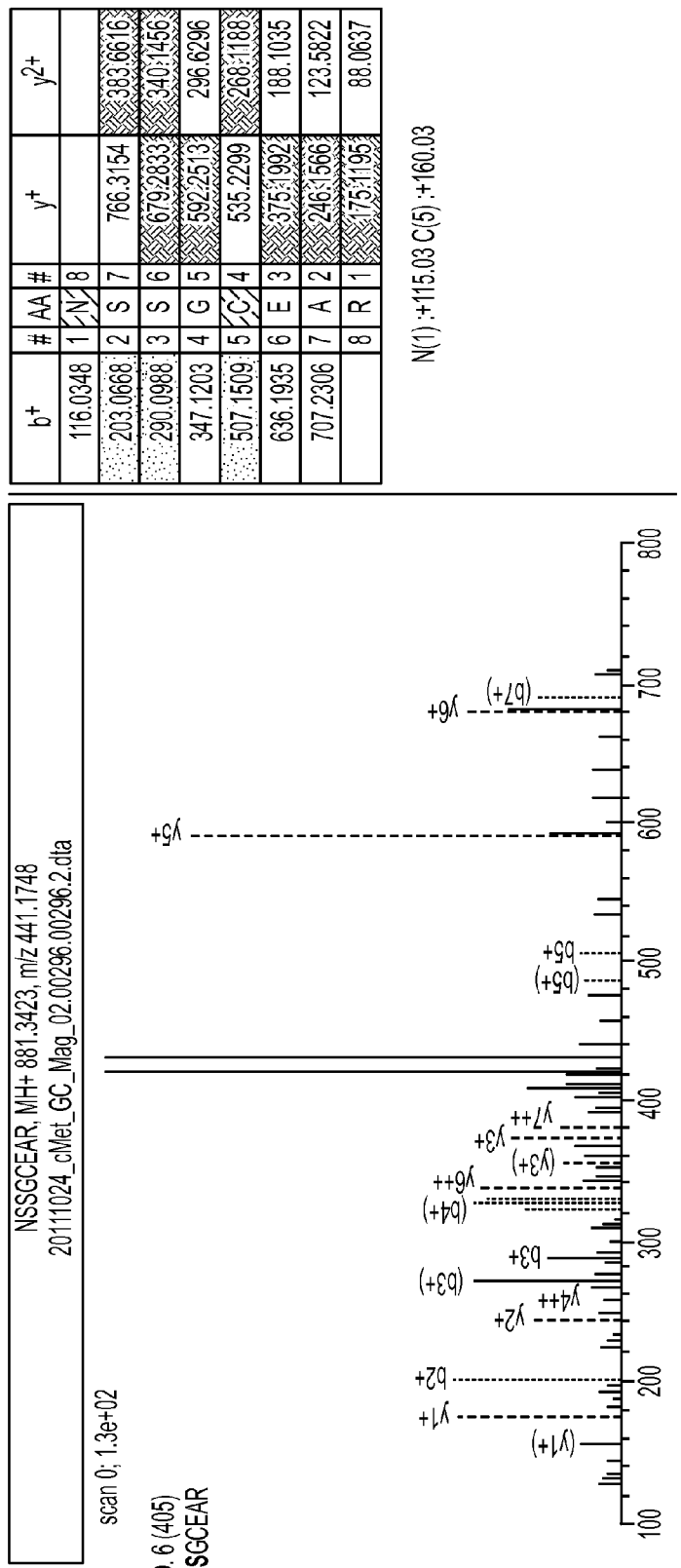
Figure 3E:
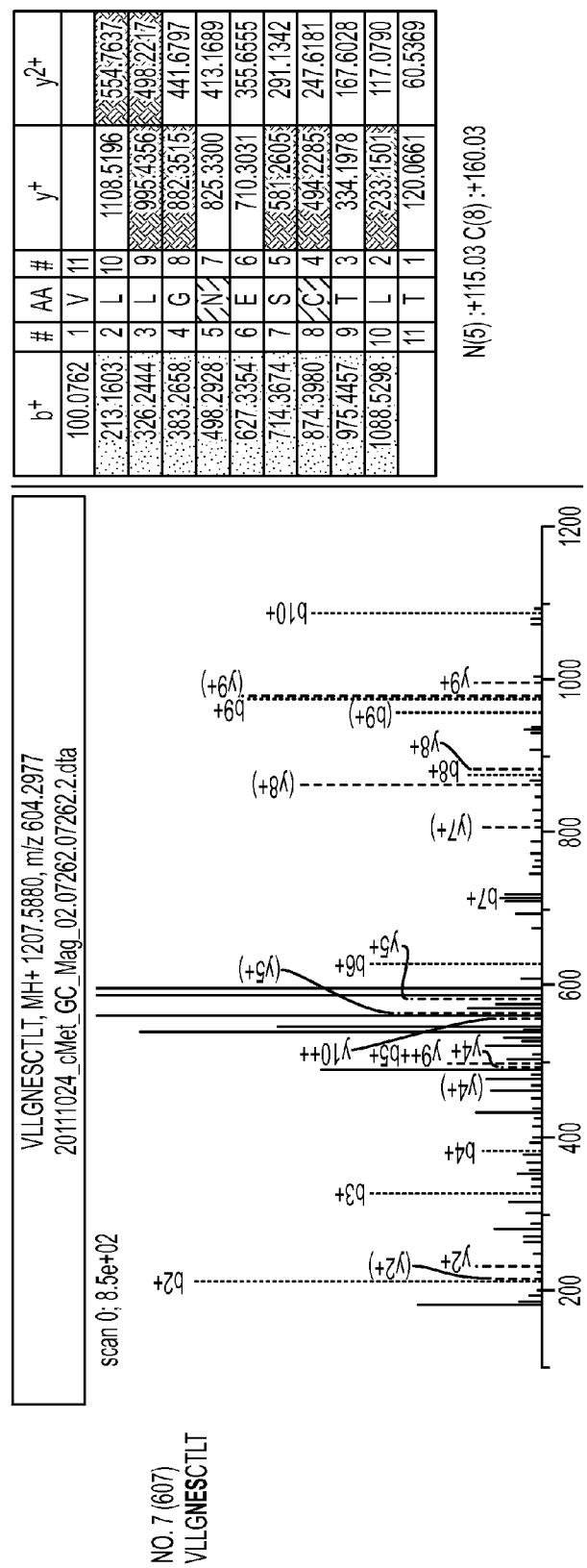
Figure 3F:
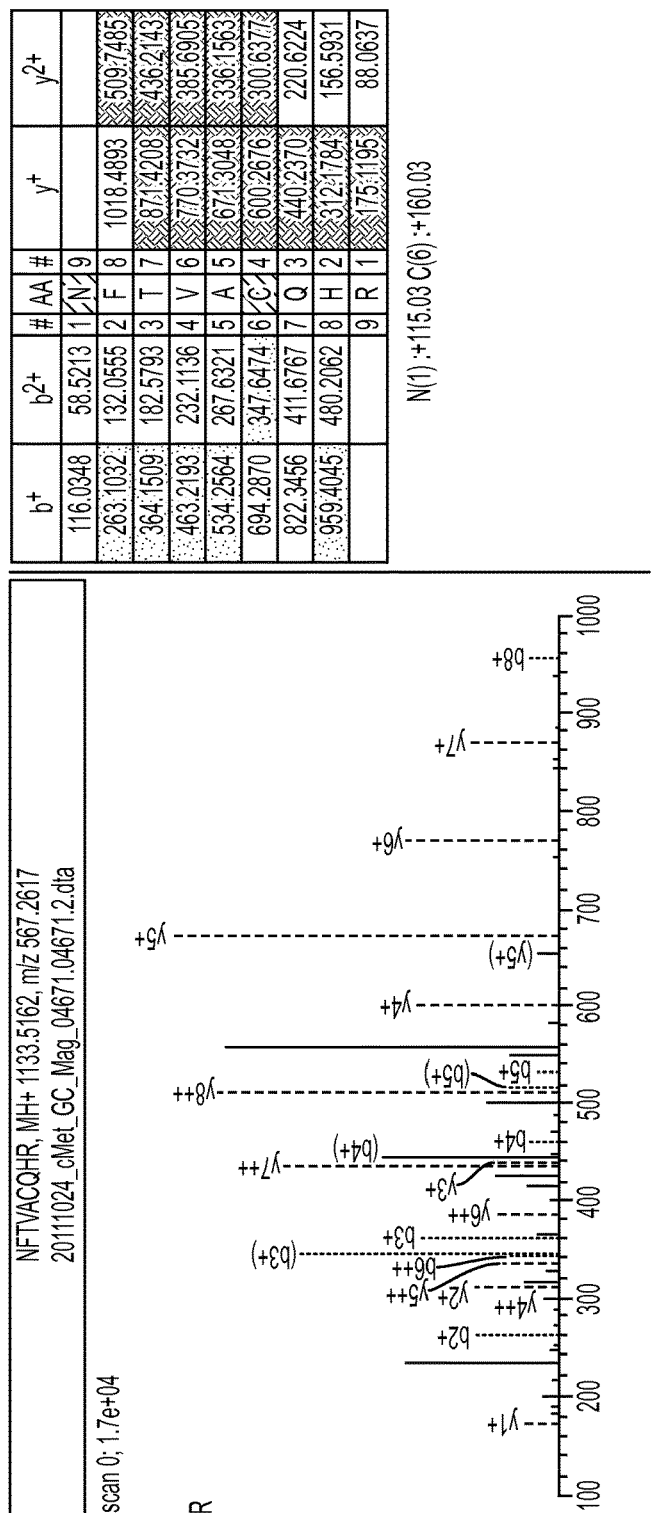

The results of the analysis are shown in FIGS. 3a to 3g. FIG. 3a shows N-linked glycosylation sites in the amino acid sequence of the human hepatocyte growth factor receptor c-MET, and FIGS. 3b to 3g show the results of LC-MS analysis of glycosylation at amino acid in positions 45, 106, 405, 607, 635 and 785 of c-MET, respectively.

1-3: Panning Using Phage Antibody Display Method

Each of a phage antibody display library ($1 \times 10^{12}$ phages/ml), hydrazide beads and c-Met-hydrazide beads was blocked in PBS/3% (w/v) non-fat milk at room temperature for at least one hour, and the phage antibody display library was mixed with the hydrazide beads, after which the hydrazide beads were captured.

The supernatant containing the phage antibodies was mixed with the c-Met-hydrazide beads and incubated at room temperature, and then the phage antibodies bound to the c-Met-hydrazide beads were captured using a magnet and washed with 1×PBS/0.1% (v/v) Tween20. Then, the phage antibodies bound to the c-Met-hydrazide beads were eluted using a glycine buffer and neutralized to a pH of 7.2-7.4 using 1M Tris (pH 8.0).

TG1 cells were transfected with the phage antibodies and then plated on a 2xYTAG (2YT containing 100 μg/mL ampicillin and 2% glucose), and each colony was isolated and incubated at 37° C. at 120 rpm for 16 hours.

1-4: Isolation of Phage Antibodies that Bind Specifically to N-Linked Glycan Binding Site of c-Met TG1 cells transfected with the phage antibodies were incubated in 2xYTAG at 37° C. at 250 rpm. When the cells were grown to the mid-log phase ($OD_{600}$), helper phages were added thereto and incubated for 1 hour. Then, the medium was replaced with a 2xYT/50 ug/ml Kan, 100 ug/ml Amp medium, and the cells were incubated at 30° C. at 250 rpm for 12-16 hours. On the following day, the cell culture was centrifuged at 4000 rpm for 10 minutes, and the supernatant containing the phage antibodies was stored to determine the binding between the phage antibodies and cMET.

1-5: Determination of Detected Antibodies

The detected phage antibodies were blocked in PBS/0.1% Tween20/3% milk (PBST/milk) at room temperature for 1 hour, and then transferred to an ELISA plate, each well of which was coated with 1-2 ug/ml cMET or a control protein. Then, the antibodies were incubated in a plate shaker at room temperature for 1-2 hours.

Then, the plate was washed six times with PBS/Tween 20, anti-fd-HRP was added to each well, and then incubation was carried out in a plate shaker at 37° C. for 1 hour. After completion of the incubation, the plate was washed 6 times in the same manner as described above, and 100 ul of a TMB substrate was added to each well and incubated with shaking. When a colorimetric reaction occurred, the absorbance of the plate at 370 nm or 620-652 nm was measured using a plate reader in order to analyze whether the antibodies bound specifically to the target. When the reaction was stopped by the addition of 100 ul of 0.25M sulfuric acid, the absorbance at 450 nm was measured.

Figure 4:
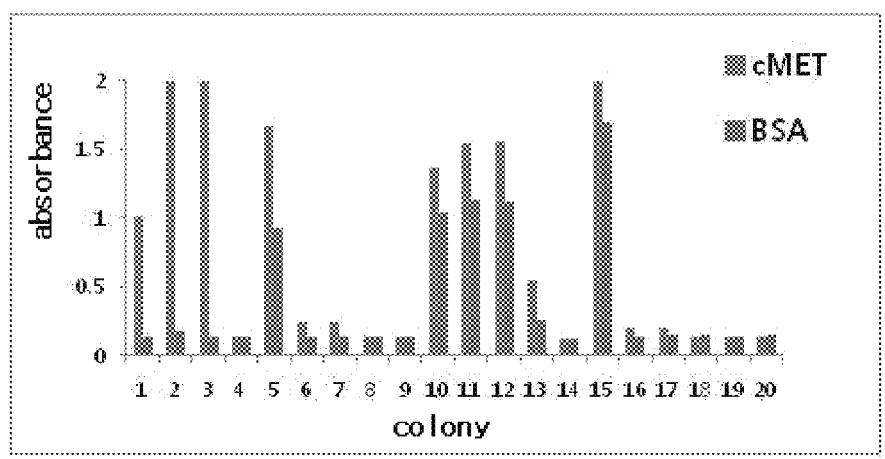
FIG. 4 shows the results of selected antibodies which bind specifically to c-MET.

FIG. 4 shows the results of a selection of antibodies (clones 1 to 3), which bound to c-MET with high specificity, using glycan-containing c-MET glycopeptide-hydrazide beads. Whether the binding of the selected antibodies to c-MET depends on the glycosylation of c-MET can additionally be analyzed by an ELISA or Western blot assay using deglycosylated c-MET.

Example 2: Production of Antibodies that Recognize as an Epitope the N-Linked Glycan Binding Site of EGFR Using recombinant human EGFR/ErbB1 (catalog No.: 1095ER) in place of c-Met protein, a monoclonal antibody that recognizes the N-linked glycan binding site of EGFR as an epitope was produced. The experimental process was carried out in the same manner as described in Example 1.

Figure 5:
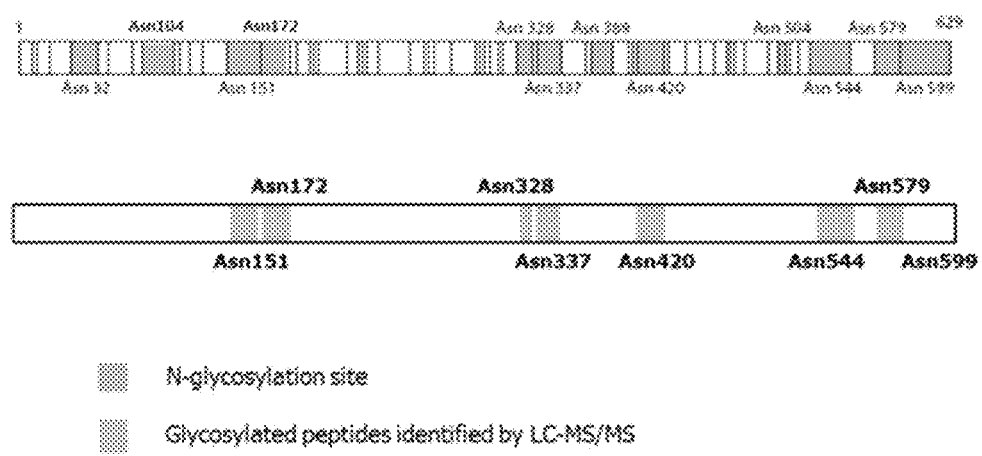
FIG. 5 is a schematic presentation of mapping N-linked glycosylated sites in recombinant human EGFR and the glycosylation sites of glycosylated peptides determined by LC-MS/MS analysis.
Figure 6A:
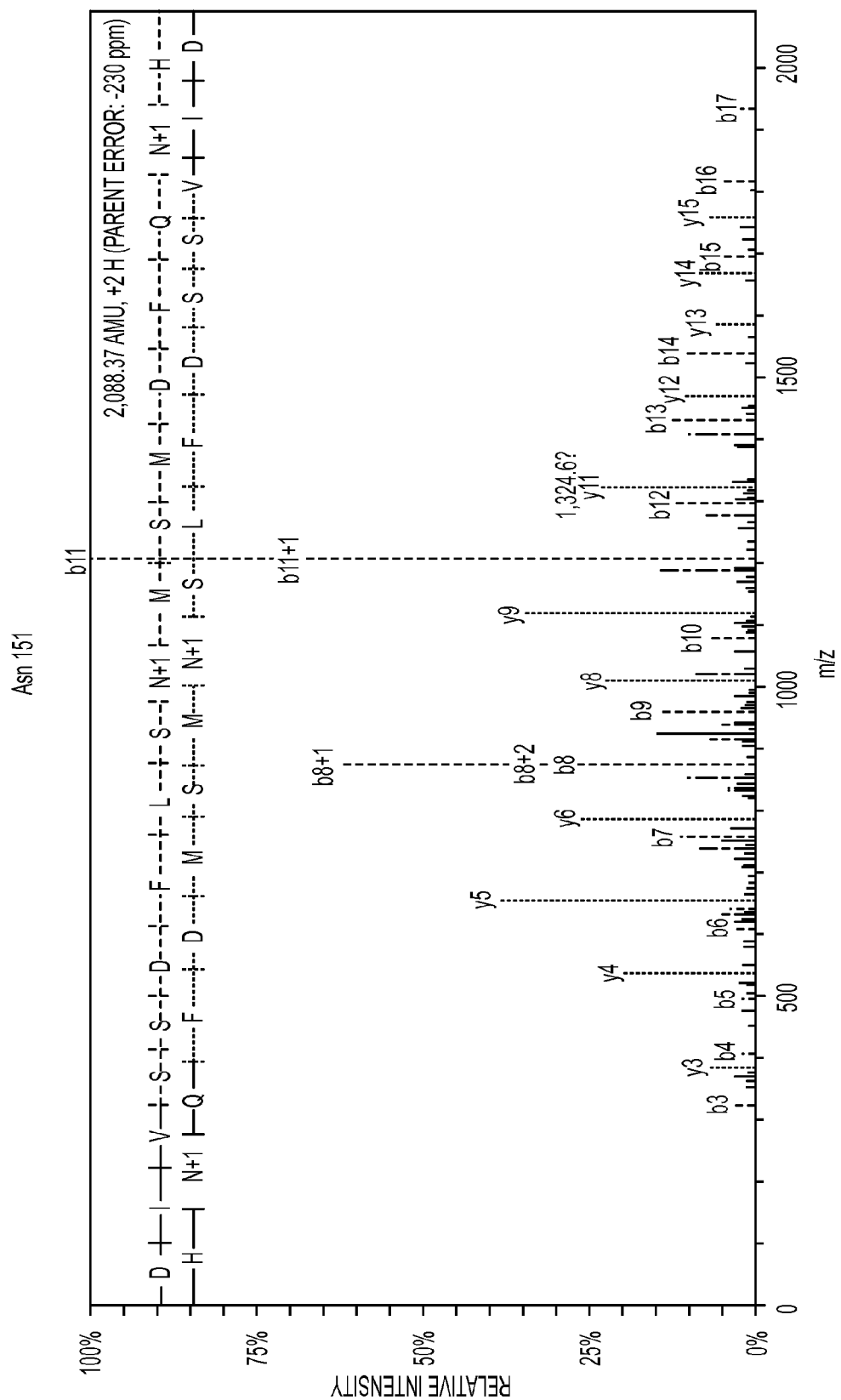
FIGS. 6A through 6G show N-linked glycosylated sites determined by the mass spectrometric analysis of the N-linked glycopeptides of human EGFR, captured using hydrazide beads.
Figure 6B:
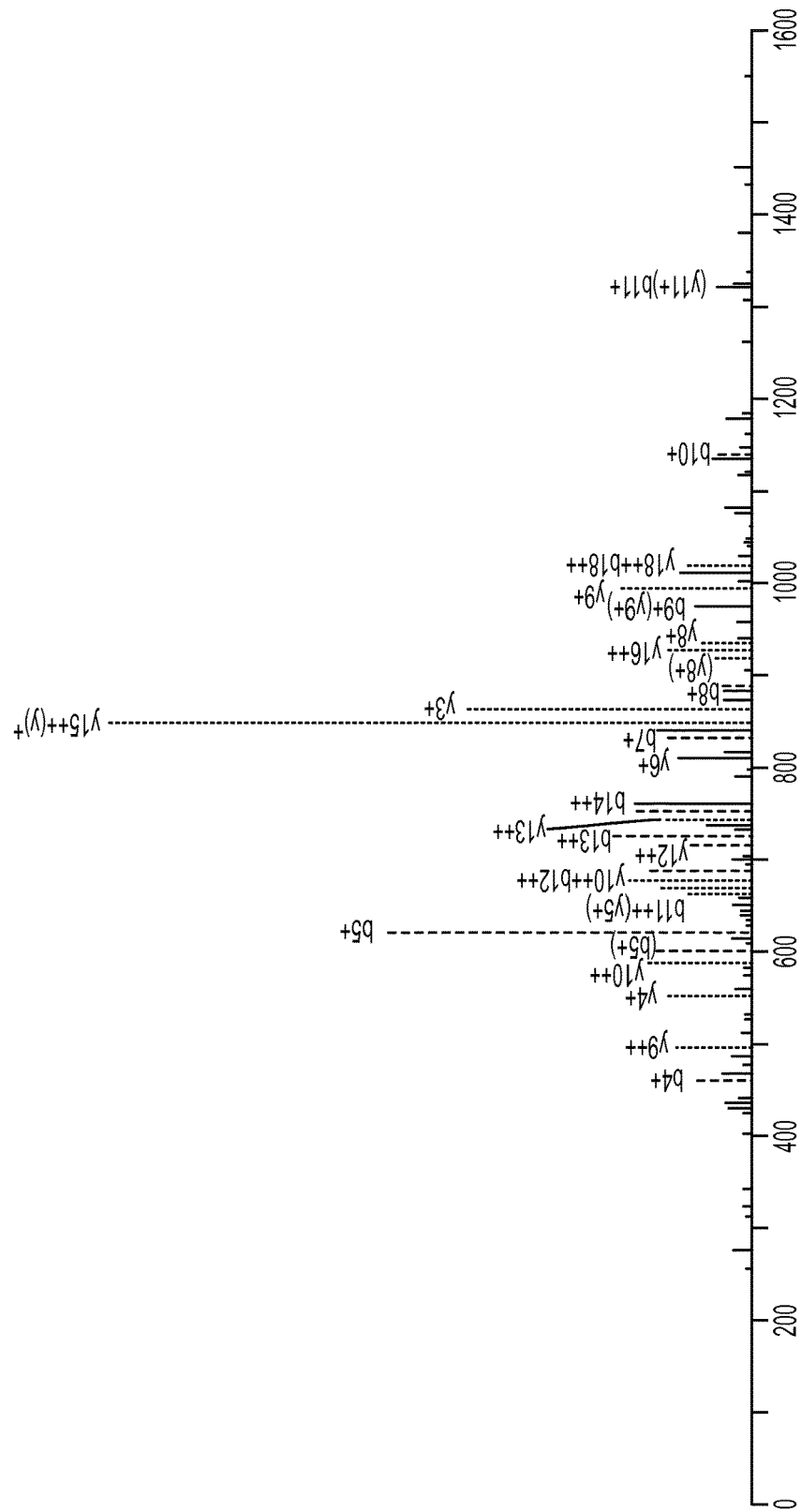
Figure 6C:
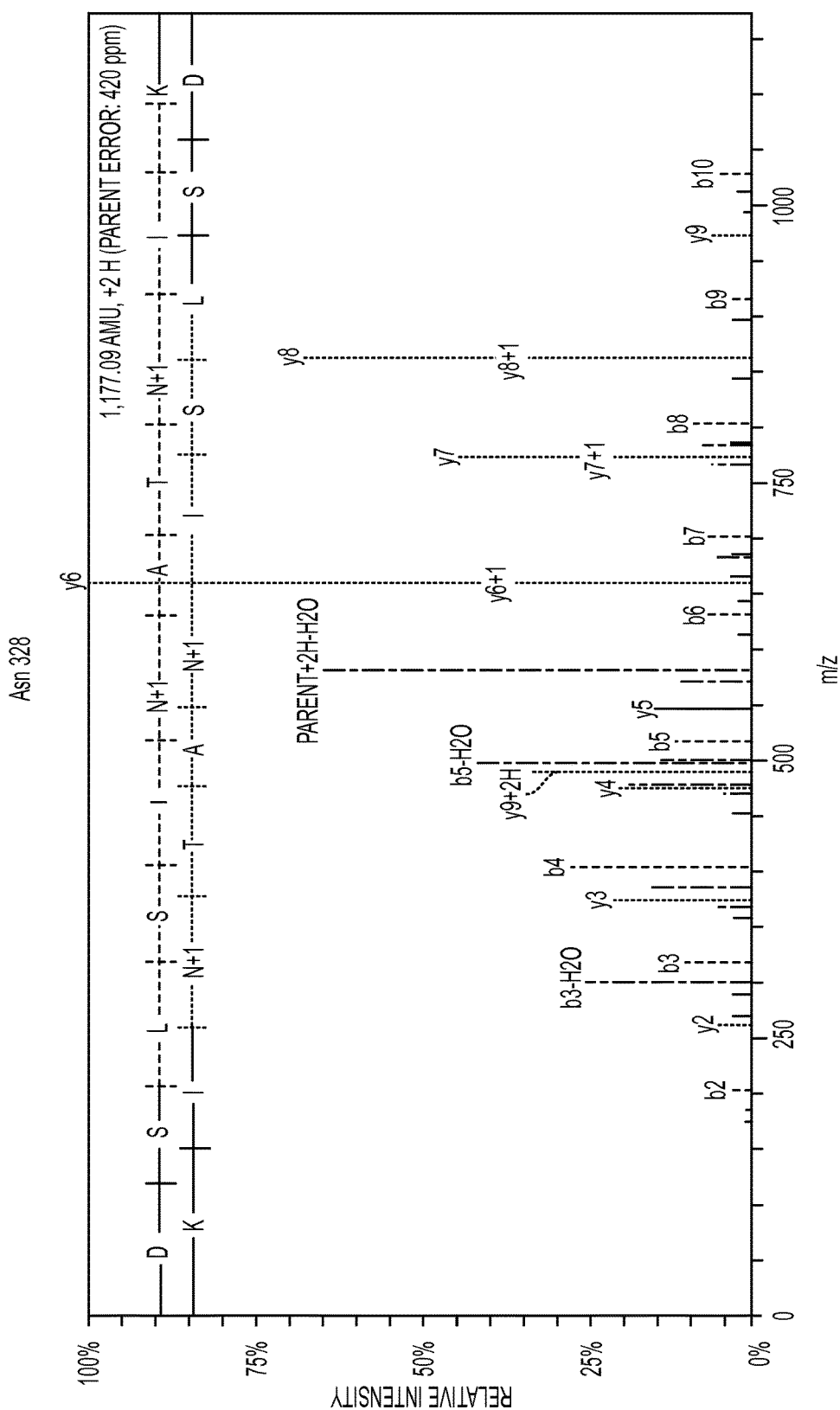
Figure 6D:
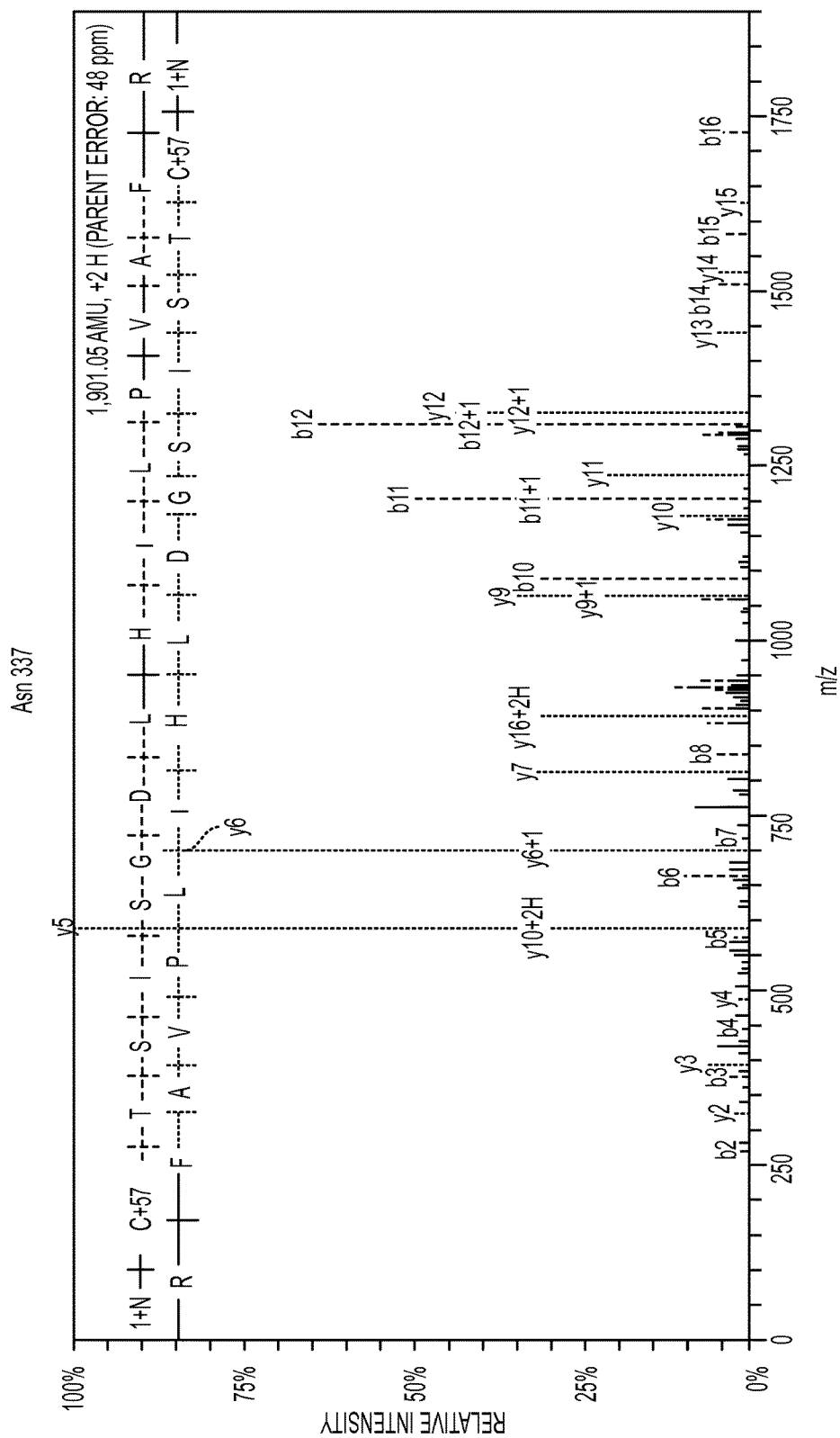
Figure 6E:
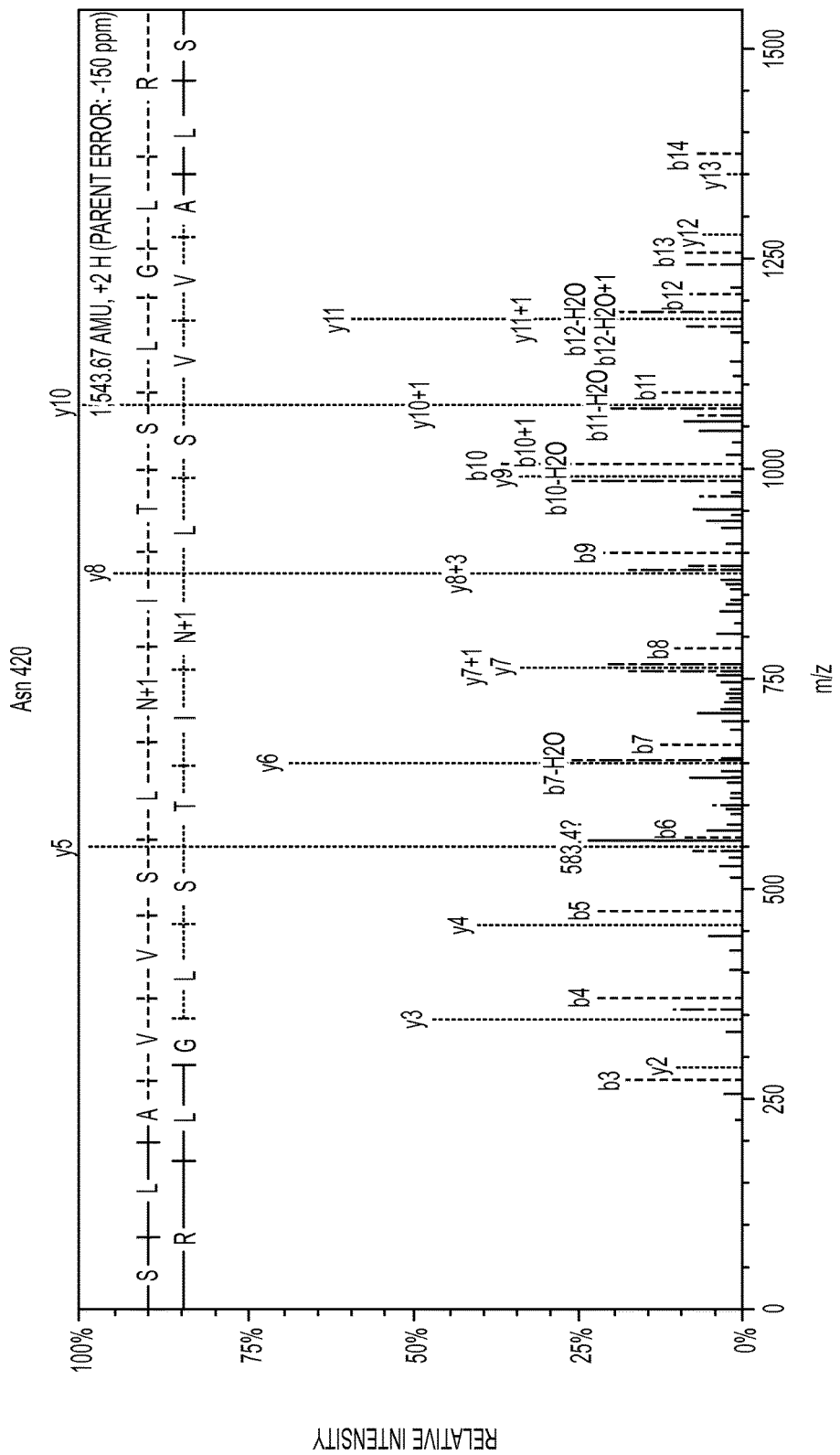
Figure 6F:
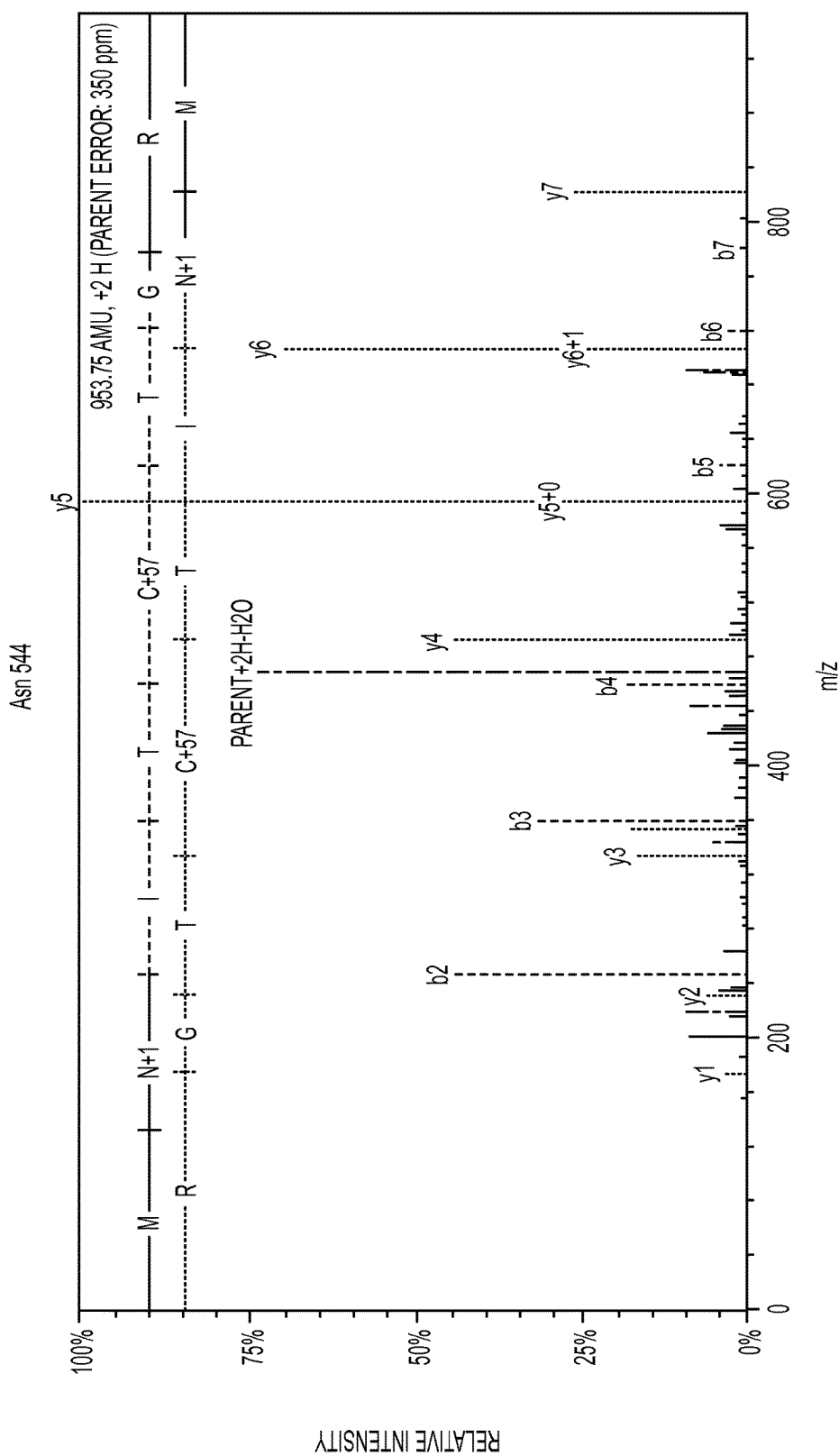
Figure 6G:
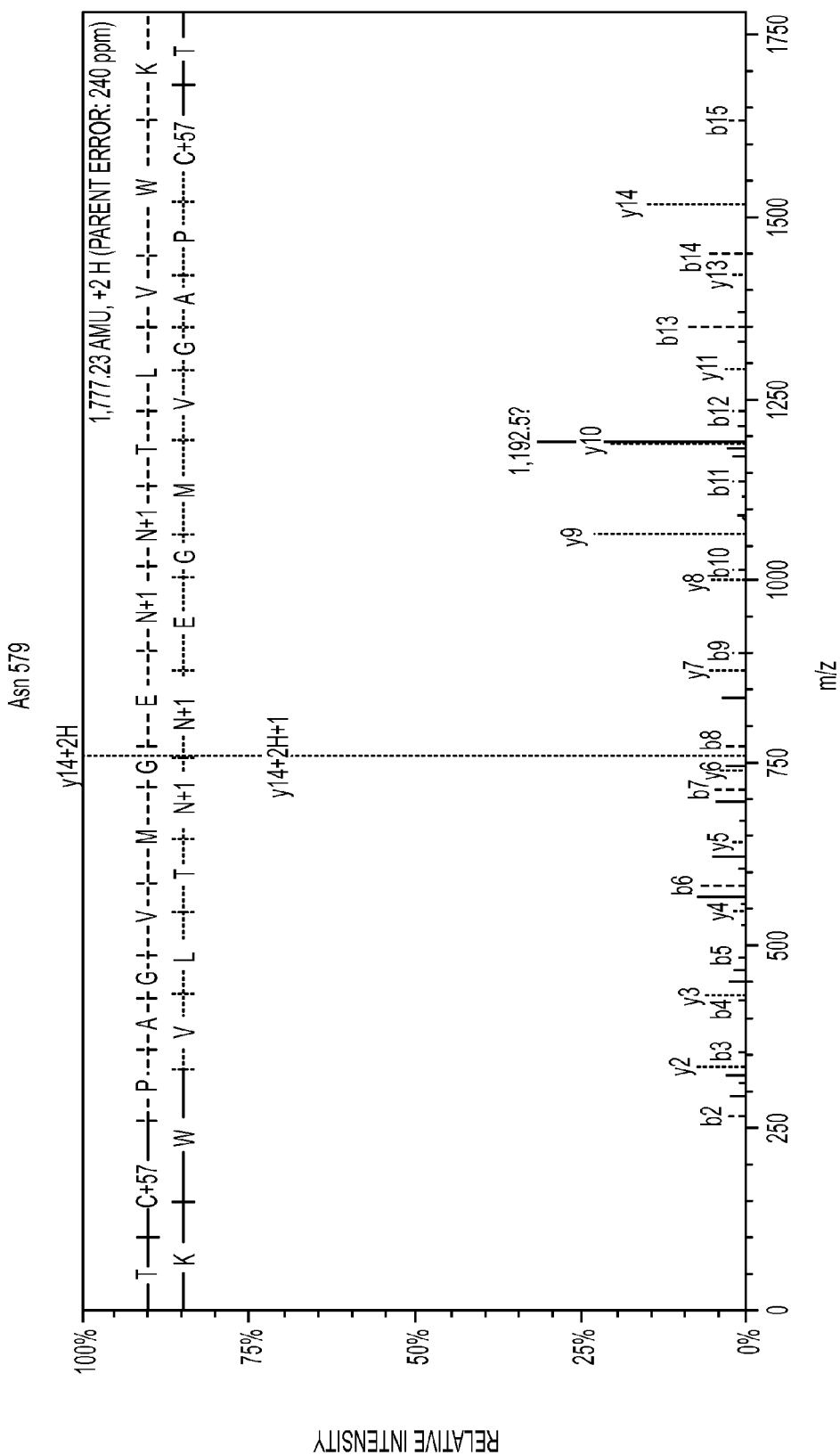

FIG. 5 is a schematic view showing the results of mapping of N-linked glycosylation sites in recombinant human EGFR and a schematic view showing the sites of glycosylated peptides determined by LC-MS/MS analysis, and FIGS. 6A through 6G show N-linked glycosylation sites determined by mass spectrometric analysis of N-linked glycopeptides of recombinant human EGFR, captured using hydrazide magnetic beads. It was shown that N-linked glycosylation sites in EGFR could be specifically selected by capturing glycopeptides using hydrazide magnetic beads.

As described above, according to the present disclosure, a monoclonal antibody that recognizes the glycan binding site of a glycoprotein as an epitope can be produced in a relatively simple and economic manner, and a monoclonal antibody having high sensitivity and specificity for the glycan binding site of a glycoprotein can be produced. The monoclonal antibody produced according to the present disclosure can be effectively used as an agent for diagnosing or treating various diseases associated with a change in glycan.

What is claimed is:

1. A method for producing a monoclonal antibody that recognizes an N-Linked glycan binding site of a glycoprotein as an epitope, the method comprising the steps of:
   a) proteolyzing the glycoprotein to obtain (poly) peptide fragments;
   b) subjecting a mixture of the (poly)peptide fragments to treatment with hydrazide to capture a glycan-containing glycopeptide;
   c) amplifying the number of phage antibodies by reacting the captured glycan-containing glycopeptide with a phage antibody display; and
   d) isolating the phage antibodies that bind specifically to the N-linked glycan binding site of glycopeptide.

2. The method of claim 1, wherein the glycoprotein shows a change in the glycan structure or expression level of glycan depending on the diagnosis of a disease, the state of a disease and the resistance of a disease to a therapeutic agent.

3. The method of claim 1, wherein step a) is performed by subjecting the glycoprotein to treatment with proteinase or a proteinase reagent.

4. The method of claim 3, wherein the proteinase is selected from the group consisting of pepsin, trypsin, chymotrypsin, peptidase, and endoproteinase GluC.

5. The method of claim 3, wherein the proteinase reagent is cyanogen bromide (CNBr).

6. The method of claim 1, wherein the method further comprises, before capturing the glycopeptide in step b), a step of desalting the (poly) peptide fragments obtained in step a).

7. The method of claim 1, wherein the method further comprises, before capturing the glycopeptide in step b), a pretreatment step of oxidizing the (poly) peptide fragments obtained in step a).

8. The method of claim 1, wherein the hydrazide beads that are used in step b) are hydrazide-terminated magnetic beads or Sepharose beads.

9. The method of claim 1, wherein the peptide, protein or scaffold library that is used in step c is selected from the group consisting of, a yeast display, a bacterial display and a ribosome display.

* * * * *